US012797558B2

(12) United States Patent
Mars et al.

(10) Patent No.: US 12,797,558 B2
(45) Date of Patent: Nov. 17, 2026

(54) PORTABLE SUBSTANCE-INJECTION DEVICE

(71) Applicant: DESVAC, Saint-Barthelemy-d'Anjou (FR)

(72) Inventors: Julie Mars, Saint-Barthelemy-d'Anjou (FR); Devan L'Haridon, Saint-Barthelemy-d'Anjou (FR); Damien Salaun, Saint-Barthelemy-d'Anjou (FR)

(73) Assignee: DESVAC, Saint-Barthelemy d'Anjou (FR)

( * ) Notice: Subject to any disclaimer, the term of this patent is extended or adjusted under 35 U.S.C. 154(b) by 427 days.

(21) Appl. No.: 18/561,775

(22) PCT Filed: May 9, 2022

(86) PCT No.: PCT/FR2022/050878
§ 371 (c)(1),
(2) Date: Nov. 17, 2023

(87) PCT Pub. No.: WO2022/243620
PCT Pub. Date: Nov. 24, 2022

(65) Prior Publication Data
US 2024/0216619 A1 Jul. 4, 2024

(30) Foreign Application Priority Data
May 18, 2021 (EP) .................................... 21305652

(51) Int. Cl.
*A61M 5/32* (2006.01)

(52) U.S. Cl.
CPC .......... *A61M 5/3287* (2013.01); *A61M 5/322* (2013.01)

(58) Field of Classification Search
CPC ...... A61M 5/3287; A61M 5/322; A61M 5/20; A61M 2005/206; A61M 2005/3114; A61M 5/16809; A61D 7/00
See application file for complete search history.

(56) References Cited

U.S. PATENT DOCUMENTS

2016/0271326 A1* 9/2016 Slate .................. A61M 5/3134
2017/0232191 A1* 8/2017 Smith .............. A61M 5/14216
604/152

(Continued)

FOREIGN PATENT DOCUMENTS

KR 102037471 B1 10/2019
WO 2016181091 A1 11/2016

OTHER PUBLICATIONS

International Search Report and Written Opinion in International Application No. PCT/FR2022/050878 mailed Aug. 11, 2022, with partial translation, 12 pages.

*Primary Examiner* — Laura A Bouchelle
*Assistant Examiner* — Marissa Taylor
(74) *Attorney, Agent, or Firm* — Victor Cardona, Esq.; Heslin Rothenberg Farley & Mesiti P.C.

(57) ABSTRACT

The present invention relates to a portable device for injecting a substance, comprising a supply circuit comprising a chamber having a first end with an outlet orifice and an open second end, a piston extending towards the inside of the chamber from the second end, the chamber having a volume that can be varied by the movement of the piston, a first electric motor (12) for moving the piston, the outlet orifice of the chamber being connected to a retractable injection needle (11) so as to supply this needle with the contents of the chamber. According to the invention, with the injection device comprising an injection-device body, the supply circuit is placed in the portable injection-device body, (Continued)

the injection-device body comprises a system for driving the needle (11) between a first position, in which the needle is housed inside the body of the injection device, and a second position, in which the needle (11) projects from the body of the injection device, the system for driving the injection needle (11) comprising a second motor (13) distinct from the first electric motor (12) so that the functions of retracting/deploying the injection needle (11) and of refilling/discharging a dose of substance are dissociated from one another.

14 Claims, 3 Drawing Sheets

(56) References Cited

U.S. PATENT DOCUMENTS

2018/0310954 A1* 11/2018 Almoumen ............. A61M 5/24
2018/0325547 A1* 11/2018 Bagwell ................. A61B 34/20

* cited by examiner

[Fig. 1]
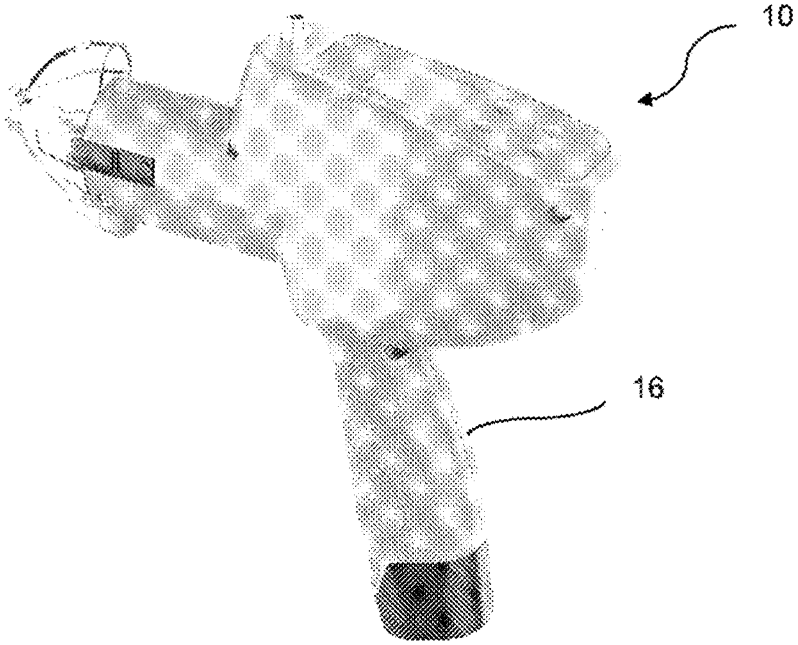
[Fig. 2]
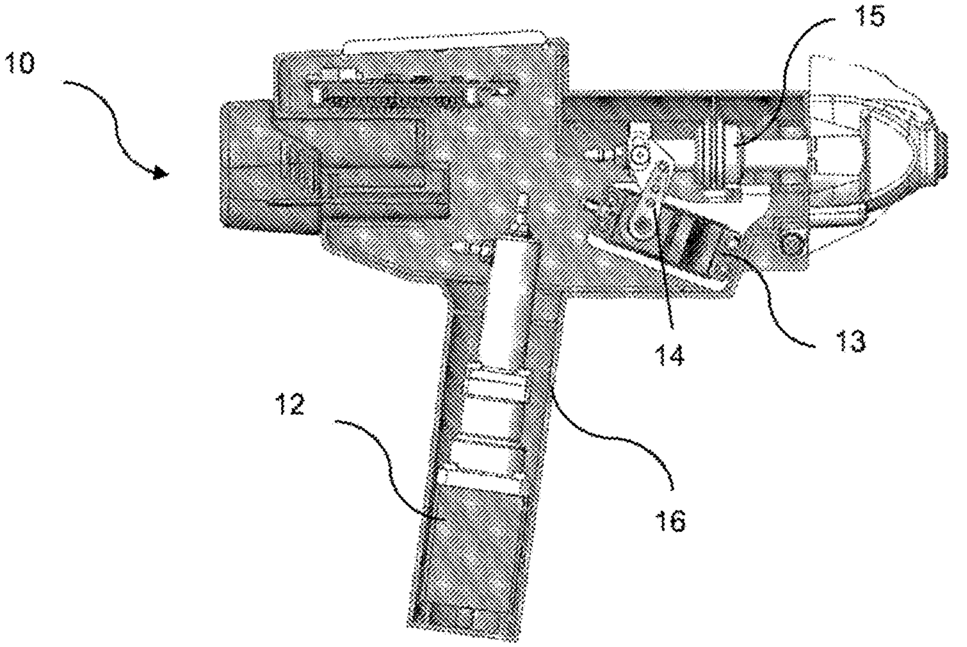

[Fig. 3]
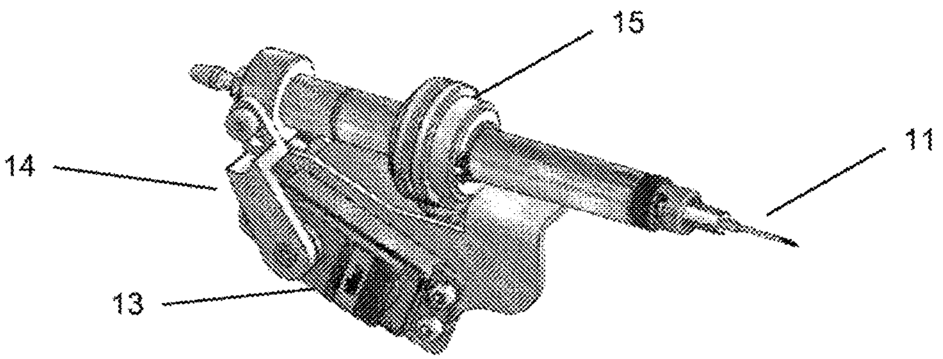
[Fig. 4]
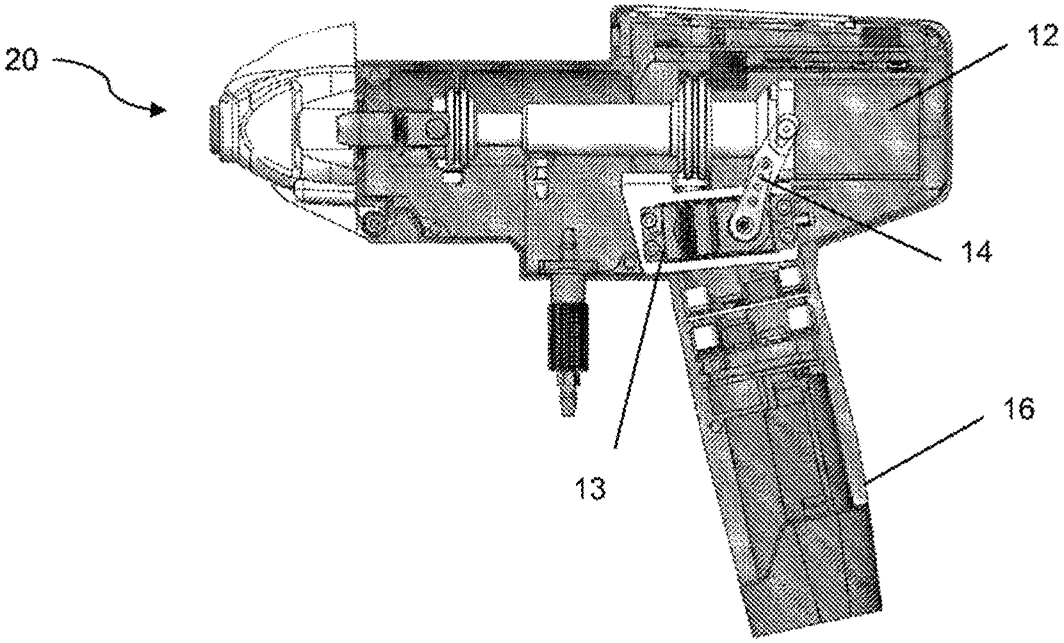

[Fig. 5]
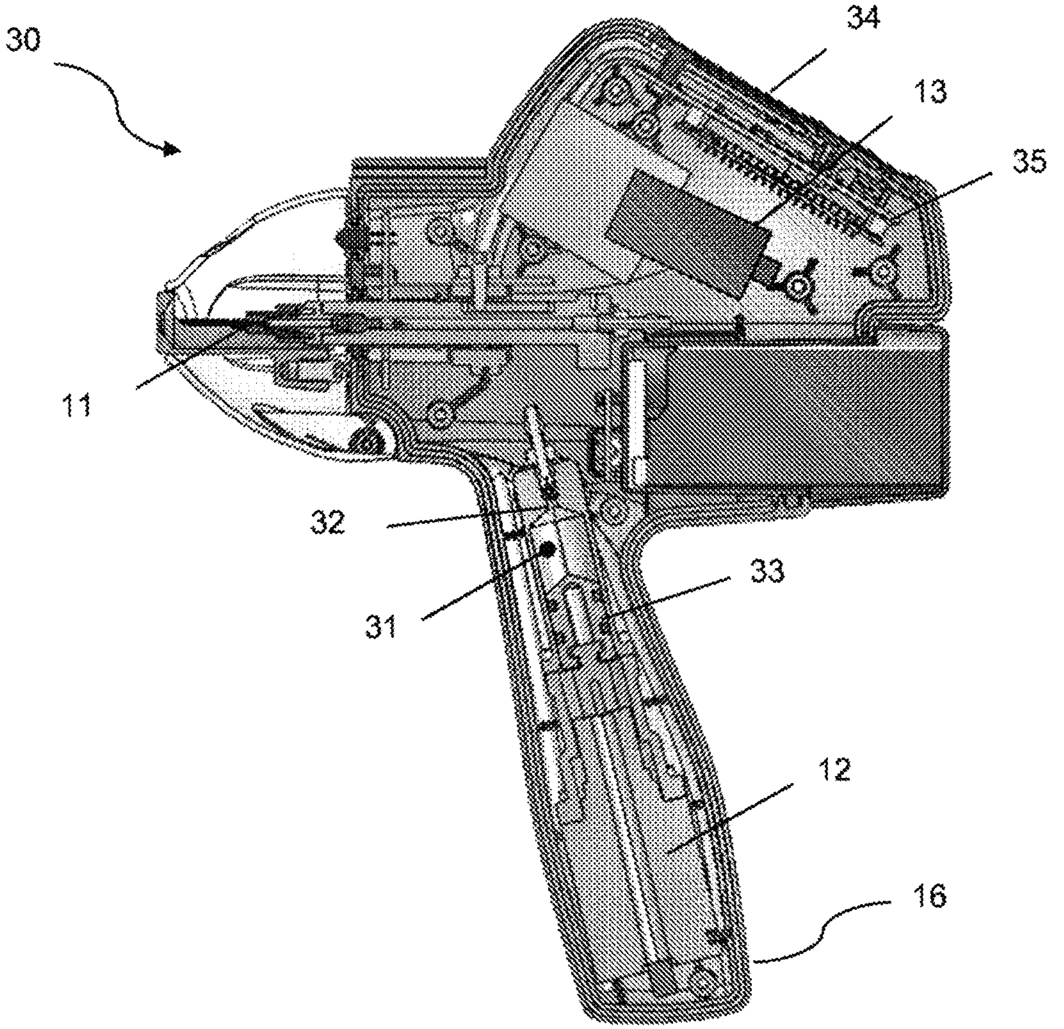

PORTABLE SUBSTANCE-INJECTION DEVICE

CROSS REFERENCE TO RELATED APPLICATIONS

This application is a U.S. National Phase filing under 35 U.S.C. § 371 of International Application PCT/FR2022/050878, filed May 9, 2022, and published as WO 2022/243620 A1 on Nov. 24, 2022. PCT/FR2022/050878 claims priority from European application number 21305652.6, filed May 18, 2021. The entire contents of each of these prior applications are hereby incorporated herein by reference.

TECHNICAL FIELD

The field of the present invention is that of devices for administering substance to one or more animals, such as dosing guns.

It more particularly relates to a portable injection device wherein the system for moving its retractable needle and the system for unloading a dose of substance through this needle are separated, the injection device also being more compact and lightweight.

It also relates to a method for managing such an injection device making it possible to treat a whole group of animals more quickly by reducing the dead time necessary for the resetting of this injection device between two successive injections.

PRIOR ART

It is known in the field of animal production to administer substances such as drugs or vaccines to groups of animals to keep them in good health.

The treatment or vaccination of the animals such as livestock, against various diseases, not only makes it possible to improve the health of these animals and to increase the profitability of a flock of animals, but is also an essential factor for the production of foodstuffs of animal origin.

It is known to administer such a substance by means of an injection gun in order to facilitate the treatment or vaccination of an entire group of animals.

Various injection guns thus exist in the prior art.

Patent application WO 2016/108187 A1 in the name of the present applicant proposes a portable injection device comprising a housing with a handle and a retractable needle housed in the housing.

This portable injection device offers reinforced safety for the operator in that it comprises a first sensor to detect the gripping of the handle of the device by a user and a second sensor to detect the presence of an animal.

This injection device further comprises a processing circuit configured to receive a first signal from the first sensor indicating that the user holds the handle and receive a second signal from the second sensor indicating that an animal is detected. The injection device deploys the needle outside the housing into the animal only when these two signals are received and delivers a dose of medicament into the animal once the needle is fully deployed into the animal.

Although it gives good results, this injection device can also be improved.

Indeed, the movement of the needle out from and into the shell of the injection device on the one hand and the discharging of a dose of substance to be delivered through this needle on the other hand are ensured by a single kinematic line comprising a single electric motor.

Additional mechanical parts such as spring pushers are then necessary to differentiate two movements, each of these movements being linked to a distinct function: the movement of the needle and the movement of the piston to discharge the contents of the chamber.

However, after each administration of a substance, it is necessary for the motor to perform a complete stroke all the way to the rear of the syringe to properly reprime the spring pushers needed at the outlet of the needle.

Furthermore, the reloading of the injection device with a new dose of substance is carried out only after the pushers have been reprimed and the motor has been stopped.

This results in a reset time of the injection device after administering a substance int an animal, which is relatively long and is responsible for a notable slowdown in the treatment operations of a whole group of animals.

Furthermore, it is known that injection devices of the prior art are heavy and are therefore likely to lead to increased operator fatigue when that person must treat a large number of animals, in particular because they must be able to use such an injection device one-handed.

There is therefore a pressing requirement for a device for administering a veterinary product to an animal such as a piglet, the original design of which makes it possible to overcome the disadvantages of the prior art described above.

SUBJECT MATTER OF THE INVENTION

The present invention aims to overcome the disadvantages of the prior art by proposing a portable substance-injection device, simple in its design and in its operating mode, whose reset, or unavailability, time after administering a substance to an animal is substantially reduced, consequently allowing faster treatment of a whole group of animals.

Another object of the present invention is such a substance injection device with a substantially reduced weight.

Another object of the present invention is such a substance injection device that is less bulky, with a center of gravity well-positioned to give the user an easy grip.

The present invention also relates to a method for managing such an injection device, making it possible to reduce the reset, or unavailability, time of this injection device between two successive administrations of a substance.

DISCLOSURE OF THE INVENTION

To this end, the invention relates to a portable substance-injection device comprising a supply circuit comprising a chamber comprising a first end with an outlet orifice and a second open end, a piston extending towards the interior of said chamber from this second end, said chamber having a volume that varies as the piston moves, a first electric motor to ensure the movement of said piston, said outlet orifice of said chamber being connected to a retractable injection needle to supply this needle with the contents of said chamber.

According to the invention, said injection device comprising an injection-device body, said supply circuit is placed in said portable injection-device body, and the injection-device body comprises a system for driving said needle between a first position, in which the needle is housed inside the body of the injection device, and a second position, in which the needle protrudes outside the body of the injection device, said system for driving said needle comprising a second motor separate from said first electric motor so that the functions of retracting/deploying the injection needle and of refilling/discharging a dose of substance, on the other hand, are dissociated.

Such an injection device advantageously makes it possible to dissociate the retractable needle drive system and the mechanical system making it possible to unload a dose of substance through this needle.

This portable injection device can be implemented to administer a substance to livestock, in particular pigs, sheep, calves, cattle, goats, etc., but also dogs and cats.

According to one embodiment of this portable substance-injection device, it comprises means for synchronizing the first and second electric motors so that the re-entry of the needle after injecting said substance and the refilling of the chamber are carried out simultaneously, or in parallel.

For example, said portable device may comprise an electronic control unit able to control both the first and second motors, said electronic control unit being configured to synchronize the first and second electric motors.

This results in significant time saved in the treatment of live animals. Tests have for example shown for a 2 mL dose of substance, 490 ms is saved over the complete cycle.

According to another embodiment of this portable substance-injection device, the first electric motor is a stepper motor.

In order to drive said piston in a translational movement inside the chamber, this stepper motor rotates a rotational/translational movement transformation system.

This rotational/translational movement transformation system is preferably a ball screw/nut system.

Alternatively, it could also be a system comprising pinions and a belt or even a pinion/rack system.

The ball screw/nut system is preferred due to its lower weight, which may represent a lightening that can be up to forty percent (40%), and preferentially thirty-four percent (34%) relative to the weight of other known drive systems.

According to yet another embodiment of this portable substance-injection device, said drive system of said needle comprises a drive member moved by a servomotor.

The implementation of a servomotor advantageously makes it possible not to overburden the injection device, the weight of this servomotor being, purely by way of illustration, of the order of only several tens of grams.

Advantageously, this drive member is a conrod/crank system. Alternatively, it could also be a pivot link.

The servomotor makes it possible to move the conrod in rotation, the latter then moving the injection needle in translation. This configuration advantageously makes it possible to limit the bulk of the drive system of the injection needle.

According to yet another embodiment of this portable substance-injection device, this injection needle being carried by said supply circuit, said drive member is connected to said supply circuit so that, when said drive member is moved by said servomotor, said supply circuit is moved into the injection-device body to move said needle between its first and second positions.

Thus, the movement of the needle between its first position and its second position is ensured by the movement of the supply circuit as a whole.

Preferably, the drive member is rigidly connected to the first motor in order to move that motor.

Advantageously, this drive member and this servomotor are placed under this supply circuit in the injection-device body.

According to yet another embodiment of this portable substance-injection device, and as an alternative to the preceding embodiment, said needle being carried by a needle support separate from said supply circuit, said drive member is connected to said needle support to move said needle between its first and second positions.

The supply circuit and the assembly comprising said needle and its own drive system are then distinct by being spaced apart from each other in the injection-device body.

Only the retractable injection needle is connected to the outlet port of the chamber by a flexible connection such as a tube, to receive the contents of this chamber during its unloading.

According to yet another embodiment of this portable substance-injection device, it comprises a gripping handle.

This gripping handle is optionally inclined, or forms an angle greater than or equal to 90°, relative to the longitudinal axis of the main body part of the injection device wherein the needle is housed and along which this needle moves.

According to yet another embodiment of this portable substance-injection device, this injection device comprising a gripping handle, the supply circuit is housed at least partially in this gripping handle.

More generally, at least a portion of the supply circuit, and in particular its chamber, is arranged non-horizontally in the portable substance-injection device when the main body part is held parallel to the floor surface.

Advantageously, such a configuration facilitates the discharge of any air pocket sucked into the supply circuit.

Furthermore, the center of gravity of the portable injection device is positioned just above the operator's wrist, giving the impression that the injection device is easy to hold.

According to yet another embodiment of this portable substance-injection device, it comprises an electronic module configured to adjust the supply signal of the coil of the first motor as a function of the resisting torque applied to the rotor of this first electric motor.

The adjustment of the supply signal, a given frequency and a given waveform, of the coil of the first electric motor to move the piston into the chamber in order to discharge same, is therefore automatic as soon as a new substance to be administered is introduced into the chamber. As an example, this supply signal is a sine wave.

According to yet another embodiment of this portable substance-injection device, said chamber is sized to determine an injection dose to be administered to an animal.

Purely by way of illustration, this chamber is a hollow cylindrical body. Preferably, the volume of said chamber is between zero (0) and ten (10) mL, preferably between zero (0) and five (5) mL. By way of example, the volume of this chamber is three (3) mL.

According to yet another embodiment of this portable substance-injection device, it comprises one or more elements chosen from among:

- a movement sensor such as an accelerometer, an inclinometer, a gyrometer,
- a temperature sensor,
- a humidity sensor,
- a time sensor such as a clock, a calendar, etc.
- a position sensor such as a GPS/GALILEO device, a geolocation device, tag, etc.
- a contactless communication device, and/or
- a wireless communication module for communicating with a network.

Preferably, this portable device is an equipment connected to a network to transmit and/or receive data.

The communications can be carried out using a local network such as Wifi, Lifi, Ethernet, etc. or a cellular access network, which may be of several types (2G, 3G, 4G, 5G), each type of network being accessible according to several cellular access technologies (2G: EDGE, GPRS, 3G: UMTS, HSDPA, HSUPA, HSPA, HSPA+, 4G: LTE, 5G).

Alternatively, it may also be a wireless communication module with low energy consumption, such as a module configured to communicate according to one of the following protocols: Bluetooth, Sigfox, LoRa, THREAD, Wifi Halow, or ZigBee.

The accelerometer can be implemented to measure the angle of inclination of the portable device during the injection of said substance into the animal. The temperature sensor can be used to measure the temperature of this substance during its injection.

The contactless communication device may be an RFID (radio frequency) reader or an NFC (Near Field communication) reader, in particular used to identify the animal bearing an individual identification tag or label.

All of this information collected from different sources can ensure the monitoring and scoring of the quality of each injection carried out.

This information can also be used to determine the number of injections made with a tank such as a bottle supplying the chamber with said substance. When a predetermined threshold value is reached, an alarm signal can be addressed to the operator to prevent the required change of the tank.

This portable substance-injection device may also comprise one or more pressure sensors to determine, for example, a contact with the animal in order to trigger the exiting of the needle and the injection.

This portable substance-injection device may further comprise a probe for measuring the level and its battery usage.

According to yet another embodiment of this portable substance-injection device, it comprises a main unit able to control said first and second motors, said main unit comprising a processor and a set of software instructions which when they are executed by said processor, make it possible to implement a method for managing a substance-injection device, wherein said needle being in its second position and the content of said chamber having been discharged, said chamber is filled with said substance during the movement of said needle from its second position to its first position.

Of course, the term "processor" is understood to mean any programmable device.

The invention also relates to a method for managing a substance injection device comprising a supply circuit comprising a chamber comprising a first end with an outlet orifice and a second open end, a piston extending towards the interior of said chamber from this second end, said chamber having a volume that varies as the piston moves, a first electric motor to ensure the movement of said piston, said outlet orifice of said chamber being connected to a retractable injection needle to supply this needle with the contents of said chamber.

According to the invention, the injection-device body comprising a system for driving said needle between a first position, in which the needle is housed inside the body of the injection device, and a second position, in which the needle protrudes outside the body of the injection device, said system for driving said needle comprising a second motor separate from said first electric motor so that the functions of retracting/deploying the injection needle and of refilling/discharging a dose of substance are dissociated, said chamber is filled with said substance during the movement of said needle from its second position to its first position.

Preferably, said chamber is completely filled with said substance to determine a new dose to be injected no later than when said needle arrives in its first position.

The present invention also relates to a computer program comprising instructions adapted to implement each of the steps of the method for managing a substance injection device, as described above, when said program is executed on a computer.

Such a computer program is downloadable from a communication network and/or recorded on a computer-readable medium and/or is executable by a processor.

The present invention further relates to the use of a substance injection device as described above for the administration to animals of active substances such as veterinary products, non-therapeutic preparations, vitamins, vaccines, etc.

BRIEF DESCRIPTION OF THE DRAWINGS

Other advantages, aims and particular features of the present invention will become apparent from the following description, made, for explanatory purposes and in no way limiting, with reference to the appended drawings, in which:

FIG. 1

FIG. 1 is a perspective view of a substance injection device according to a particular embodiment of the present invention;

FIG. 2

FIG. 2 is a sectional view of the injection device of FIG. 1 showing the arrangement of the drive system of the injection needle and that of the circuit for supplying said needle within the injection-device body;

FIG. 3

FIG. 3 is a perspective view of the system for driving the injection needle of the injection device of FIG. 1;

FIG. 4

FIG. 4 is a sectional view of an injection device according to a second embodiment of the present invention, the arrangement of the drive system of the injection needle and the arrangement of the supply circuit of said needle within the injection-device body being visible;

FIG. 5

FIG. 5 is a sectional view of an injection device according to a third embodiment of the present invention;

DESCRIPTION OF EMBODIMENTS

The drawings and the following description essentially contain elements of a certain nature. They may therefore not only serve to better understand the present invention, but also contribute to its definition, where appropriate.

First, it should be noted that the figures are not to scale.

FIGS. 1 to 3 schematically illustrate a portable substance-injection device according to a first embodiment of the present invention.

This injection device 10 comprises a retractable needle 11 for the injection of a substance into an animal, here a piglet. In a known manner, this injection needle 11 is a hypodermic needle made of stainless steel.

This injection device 10 comprises a fluid supply circuit for discharging a dose of a substance to be delivered through this injection needle 11.

This supply circuit (partially shown) comprises a chamber that here has a hollow cylindrical body, which comprises a first end with an outlet orifice emerging onto a pipe in fluid communication with the inner channel of the injection needle 11 and a second open end, a piston extending towards the inside of this chamber from this second end.

The periphery of the piston head which is also cylindrical, ensures fluid-tightness with the inner wall of the chamber. This chamber thus has a variable volume by moving the piston therein.

The maximum volume of this chamber defines a dose of substance to be administered to the piglet, such as a 3 mL dose.

To ensure the movement of this piston, inside the chamber, the injection device comprises a stepper motor 12. This stepper motor 12 rotates a rotational/translational movement transformation system which is here a ball screw/nut system.

Thus, this drive unit comprising the stepper motor 12 and the ball screw/nut system makes it possible to move the piston in translation inside the chamber in order to vary its volume and discharge its contents through the injection needle 11.

The system for driving the injection needle 11 comprises, for its part, a servomotor 13, which produced enough torque to nose the needle 11 into the shoulder of the piglet.

The system for driving the injection needle 11 and the system for unloading a dose of substance through this injection needle 11 therefore each comprise a motor of their own.

In order to move the injection needle 11 between its first position and its second position, the servomotor 13 rotates a drive member which is here a conrod/crank system 14. A bearing 15 ensures the linear movement of the injection needle 11 between its two extreme positions.

The supply circuit comprising the first electric motor 12, the screw/nut system, the piston and the chamber, is here advantageously housed in the gripping handle 16 of the injection device 10.

An immediate advantage of this arrangement is that, the supply circuit being arranged in the shell of the injection device 10 non-horizontally but with its chamber directed upward, it is easier to drive out any air bubbles that would have been sucked into the supply circuit.

In addition, such a configuration allows greater compactness of the injection device 10 while ensuring better grip for the user, the center of gravity of the system being better positioned.

Thus, it is observed that the original design of the injection device shown in FIGS. 1 to 3 ensures greater compactness and reduced weight to the latter, which leads to less fatigue for the operator when performing their tasks.

FIG. 4 is a sectional view of a portable substance-injection device according to a second embodiment of the present invention.

The elements bearing the same references as those shown in FIGS. 1 to 3 represent the same objects, which will not be described again below.

The portable injection device 20 of FIG. 4 differs from that shown in FIGS. 1 to 3 in that the servomotor 13 and the conrod/crank assembly 14 are arranged in the main body of this portable device under the supply circuit. The conrod/crank assembly 14 thus connects the servomotor 13 to the first electric motor 12 so that the rotational movement of the conrod by the servomotor 13 causes a translational movement of the first electric motor 12 inside the space defined by the shell of the injection device 20.

The translational movement of the first electric motor 12 to which the rest of the injection circuit of the injection needle is connected, this circuit also carrying the injection needle 11, makes it possible to move this injection needle out from and into the shell of the portable injection device 20.

FIG. 5 is a sectional view of a portable injection device 30 according to a third embodiment of the present invention.

The elements bearing the same references as those shown in FIGS. 1 to 3 represent the same objects, which will not be described again below.

This injection device 30 comprises a fluid supply circuit for discharging a substance to be injected through its injection needle 11.

This supply circuit (partially shown) comprises a chamber 31 that here has a hollow cylindrical body, which comprises a first end with an outlet orifice 32 emerging onto a pipe (not shown) in fluid communication with the inner channel of the injection needle 11 and a second open end, a piston 33 extending towards the inside of this chamber 31 from this second end.

This portable injection device 30 also comprises a display screen 34 enabling the operator to select functions from a menu. An electronic module 35 provided with a processor makes it possible to manage the display and the software making it possible to operate the injection device 30.

The invention claimed is:

1. A portable substance-injection device comprising:

a supply circuit comprising a chamber comprising a first end with an outlet orifice and a second open end, a piston extending towards the interior of said chamber from this second end, said chamber having a volume that varies as the piston moves, a first electric motor to ensure the movement of said piston, said outlet orifice of said chamber being connected to a retractable injection needle to supply this needle with the contents of said chamber, said injection device comprising an injection-device body, said supply circuit placed in said portable injection-device body, the injection-device body comprising a drive system for driving said needle between a first position, in which the needle is housed inside the body of the injection device, and a second position, in which the needle protrudes outside the body of the injection device, said system for driving said needle comprising a second motor separate from said first electric motor so that functions of retracting/deploying the injection needle and of refilling/discharging a dose of substance, are dissociated; and means for synchronizing the first and second electric motors so that the needle moves to the first position from the second position by the second motor after injection of said substance and the chamber is filled by the first motor simultaneously.

2. The portable substance-injection device according to claim 1, wherein the first electric motor is a stepper motor.

3. The portable substance-injection device according to claim 1, wherein said drive system of said injection needle comprises a drive member moved by said second motor said second motor being a servomotor.

4. The portable substance-injection device according to claim 3, wherein said drive member is a conrod/crank system.

5. The portable substance-injection device according to claim 3, wherein said injection needle is carried by said supply circuit, said drive member is connected to said supply circuit so that, when said drive member is moved by said second motor, said supply circuit is moved into the injection-device body to move said needle between its first and second positions.

6. The portable substance-injection device according to claim 5, wherein said drive member is rigidly connected to the second motor.

7. The portable substance-injection device according to claim 3, wherein said injection needle is carried by a needle support separate from said supply circuit, said drive member is connected to said needle support to move said needle between its first and second positions.

8. The portable substance-injection device according to claim 1, further comprising a gripping handle.

9. The portable substance-injection device according to claim 1, wherein a chamber of the supply circuit is arranged non-horizontally in the portable injection device when a main body part is held parallel to a floor surface.

10. The portable substance-injection device according to claim 1, further comprising an electronic module configured to adjust a supply signal of a coil of the first motor as a function of a resisting torque applied to a rotor of the first electric motor.

11. The portable substance-injection device according to claim 1, wherein said chamber is sized to determine an injection dose.

12. The portable substance-injection device according to claim 1, further comprising one or more elements selected from a motion sensor, a temperature sensor, a humidity sensor, a time sensor, a position sensor, a contactless communication device and/or a wireless communication module for communicating with a network.

13. A method for managing a substance-injection device comprising a supply circuit comprising a chamber comprising a first end with an outlet orifice and a second open end, a piston extending towards the interior of said chamber from this second end, said chamber having a volume that varies as the piston moves, a first electric motor to ensure the movement of said piston, said outlet orifice of said chamber being connected to a retractable injection needle to supply this needle with the contents of said chamber, the injection-device body comprising a system for driving said needle between a first position, in which the needle is housed inside the body of the injection device, and a second position, in which the needle protrudes outside the body of the injection device, said system for driving said needle comprising a second motor separate from said first electric motor so that the functions of retracting/deploying the injection needle and of refilling/discharging a dose, are dissociated, and filling said chamber with said substance by the first motor during the movement of said injection needle by the second motor from the second position to the first position.

14. The method for managing a substance-injection device according to claim 13, wherein the filling said chamber with said substance comprises completely filling said chamber with said substance to determine a dose to be injected no later than when said injection needle arrives in the first position.

* * * * *